United States Patent [19]
Ahmed

[11] Patent Number: 5,182,268
[45] Date of Patent: Jan. 26, 1993

[54] PHARMACEUTICAL COMPOSITION COMPRISING DAUNORUBICIN POTENTIATED WITH 2,4,5-TRI(4-METHOXYPHENYL)-4,5-DIHYDROIMIDAZOLE

[75] Inventor: Nahed K. Ahmed, Prairie Village, Kans.

[73] Assignee: Marion Merrell Dow, Inc., Cincinnati, Ohio

[21] Appl. No.: 737,570

[22] Filed: Jul. 26, 1991

Related U.S. Application Data

[63] Continuation of Ser. No. 440,122, Nov. 22, 1989, abandoned.

[51] Int. Cl.$^5$ .............. A01N 43/04; A01N 43/42; A61K 31/33; A61K 31/70
[52] U.S. Cl. .................... 514/39; 514/183; 514/185; 514/283; 514/400
[58] Field of Search ............ 514/39, 171, 183, 185, 514/201, 283, 399, 400, 459

[56] References Cited

PUBLICATIONS

Zimmerman et al., Proc. Annu. Meeting of the Am. Cancer Society 25: p. 351 (1984)–Abstract 1393.
Zupanc, et al. Glasmk Hemicara I Technologa BiH. Sarajevo 27/28 (1980–1981) Bull Soc. Chem. and Technolog, Sarajevo, p. 71–80.
Williams et al., Jacs 1959, 21(3): 4464–4469.
Honn et al., *Biochem Pharm.* 34: pp. 235–241 (1985), "Ihibition by Dithydropyridine Class Calcium Channel Blockers of Tumor Cell–Platelet–Endothelial Cell Inter Actions in Vitro and, in Vivo Metastases."
Tsuruo et al., *Cancer Chemother. Pharmacol.* 14: pp. 30–33 (1985), "Inhibition of Spontaneous and Experimental Tumor Mestasis by the Calcium Antogonist Nerapamil".
Onoda et al., *Cancer Lett.* 30: pp. 181–188 (1986), "Cisplatin with Nifidipine: Synergistic Cytoxicity Against Murine Solid Tumors and Their Metatases".
Onoda et al., *Proc. Annu. Meet. Am. Assoc. Cancer Res.* 25: p. 351 (1984), "Antimetastic Effect of the Calcium Channel Blocker Diltiazem".
Honn et al., *Proc. Soc. Exp. Biol. Med.* 174: pp. 16–19 (1983), "Calcium Channel Blockers: Potential Antimetastatic Agents".
Honn et al., *Treatment of Metastasis: Problems and Prospects,* pp. 259–262 (1984) "Antimetastatic Therapy with Calcium Active Compounds".
Pauwels-Veraghy et al., *Fourth European Conference on Clinical Oncology and Cancer Nursing,* Madrid, Nov. 1–4, 1987 Federation of European Cancer Societies, 1987, p. 88.
Bessho et al., *Medical and Pediatric Oncology,* 13: pp. 199–202 (1985), Treatment of Children with Refractory Acute Lymphotic Leukemia with Vincristine and Diltiazem.
Ahmed et al., *Eur. J. Cancer Clin. Oncol.,* 23: pp. 1329–1336 (1987), "Characterization of Daunorubin Resistance in K562 Leukemia Cells Lacking Daunorubin Reductase Activity".
Helson, *Cancer Drug Delivery,* 1: pp. 353–361 (1984), "Calcium Channel Blocker Enhancement of Anticancer Drug Cytoricity"–A Review.
Tsurno et al., *Cancer Research,* 43: pp. 2905–2910 (1983), "Circumvention of Vincristine and Andriamycin Resistance in Vitro and in Vivo by Calcium Influx Blockers".

*Primary Examiner*—Nathan M. Nutter
*Attorney, Agent, or Firm*—Neal O. Willmann

[57] ABSTRACT

2,4,5-Tri(4-methoxyphenyl)-4,5-dihydroimidazole, or a pharmaceutically acceptable salt thereof, is employed as a cancer drug potentiator or as an antimetastis drug.

1 Claim, 1 Drawing Sheet

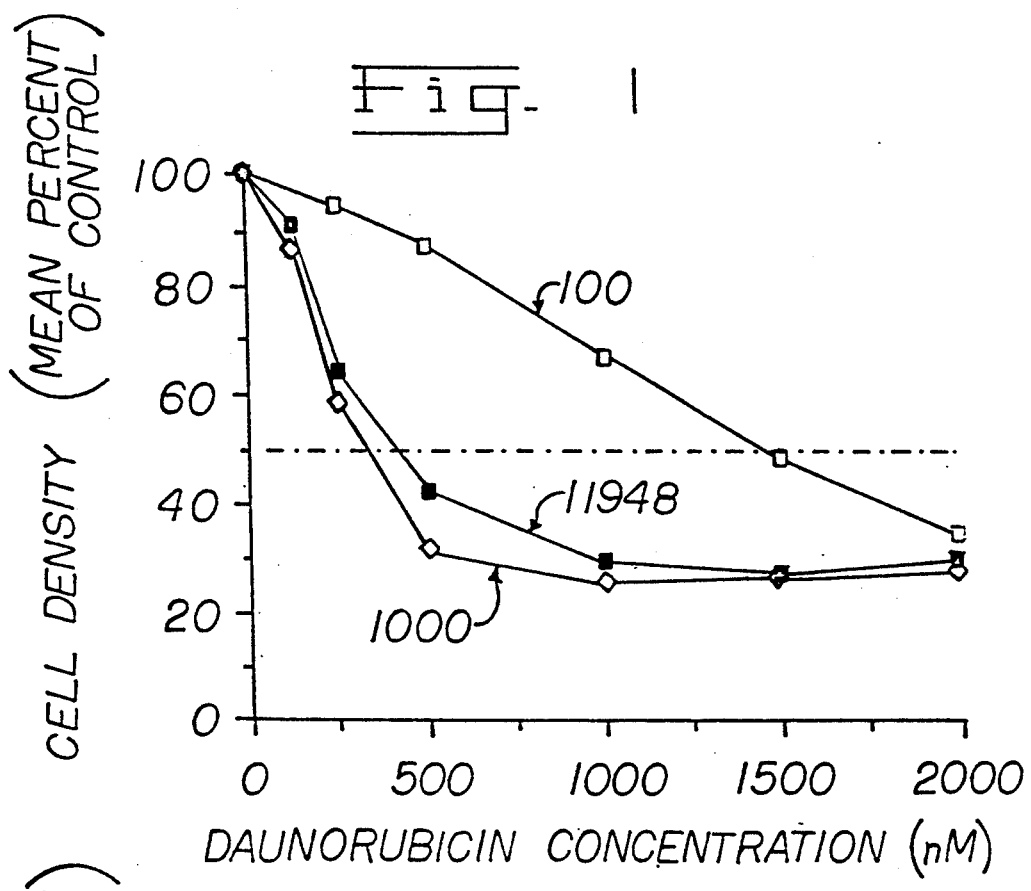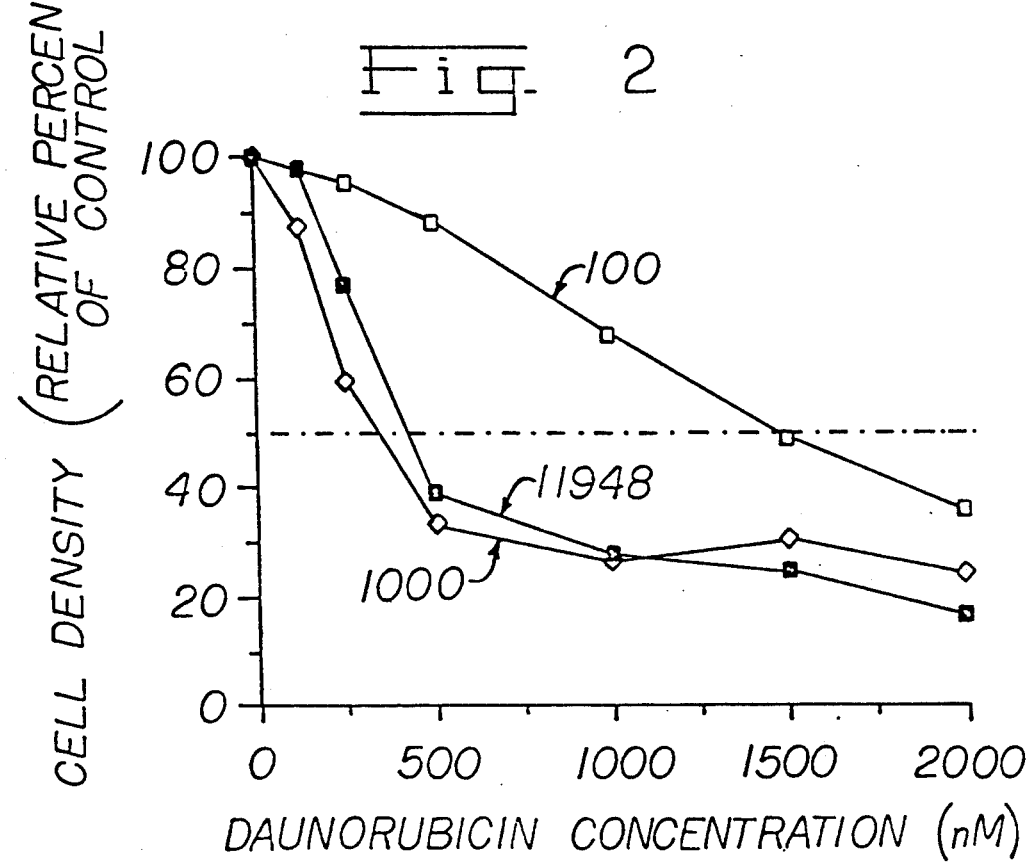

PHARMACEUTICAL COMPOSITION COMPRISING DAUNORUBICIN POTENTIATED WITH 2,4,5-TRI (4-METHOXYPHENYL)-4,5-DIHYDROIMIDAZOLE

CROSS-REFERENCE TO RELATED APPLICATION

This is a continuation of application Ser. No. 07/440,122, filed Nov. 22, 1989, now abandoned.

FIELD

This invention concerns cancer treatments.

BACKGROUND

The expression and proliferation of drug-resistant tumor cells, i.e., tumor cells which cytotoxic agents have no appreciable ability to kill at concentrations that are tolerable to normal host tissue, are considered to be a major cause of failure in cancer chemotherapy. Generally, resistance is acquired through multiple mechanisms under the selection pressure of chemotherapy. Multi-drug resistance (MDR) characterizes a complex cell phenotype, the predominant feature of which is resistance to a wide range of cytotoxic agents, many of which are anti-cancer drugs. The in vivo MDR can be mimicked in vitro by developing and selecting resistant mammalian cell lines. Although resistance is developed to a single drug, the cells show cross-resistance to a variety of structurally unrelated compounds. The factors underlying the development of resistance are multiple and include: 1) over-expression of a membrane glycoprotein, gp 170; 2) alteration in drug uptake; 3) alteration in drug binding to target sites; 4) increased efflux of drug; 5) alteration in cellular metabolism resulting in activation or inactivation of drug, and 6) alterations in DNA repair mechanisms.

Despite the complexity of MDR and the heterogeneity of tumor cells, some calcium channel blockers, e.g., verapamil (perhaps the most studied for clinical application), diltiazem, nicardipine and nifedipine, phenothiazines, and calmodulin inhibitors as agents to enhance resistant cells chemosensitivity have been studied. See e.g. Helson, *Cancer Druo Delivery* 1:353-61 (1984); Tsurno et al., *Cancer Research* 43:2905-10 (1983); Bessho et al., *Medical and Pediatric Oncology* 13:199-202 (1985).

Also, metastasis, in cancer, the appearance of neoplasms in parts of the body remote from the seat of the primary tumor, is a problem recurring in cancer treatment. It results from dissemination of tumor cells by the lymphatics or blood vessels, or through serous cavities or subarachnoid or other spaces, and if widespread, usually renders the cancer incurable by surgery alone.

Some literature in the art reports that calcium channel blockers may represent a new class of antimetastatic agents with several attractive features, including low chronic toxicity, oral administration capability, clinical trial stage research, and/or already approved for cardiovascular disease. See e.g., Honn et al., *Biochem Pharm.* 34:235-41 (1985); Tsuruo et al., *Cancer Chemother. Pharmacol.* 14:30-3 (1985); Onoda et al., *Cancer Lett.* 30 181-8 (1986); Onoda et al., *Proc. Annu. Meet. Am. Assoc. Cancer Res.* 25:351 (1984); Honn et al., *Proc. Soc. Exp. Biol. Med.* 174:16-9 (1983); Honn et al., "Treatment of Metastasis: Problems and Prospects," London, Taylor and Francis, (1984) pp. 259-62; Pauwels-Vergely et al., Fourth European Conference on Clinical Oncology and Cancer Nursing, Madrid, Nov. 1-4, 1987, Federation of European Cancer Societies, 1987, p. 88.

Still, the art lacks and needs improved cancer drug potentiators. The art lacks and needs further treatments for metastasis.

SUMMARY

Provided, in one aspect, is a method of potentiating an anti-cancer drug effect in a subject comprising administering to the subject in general concurrence amounts of 2,4,5-tri(4-methoxyphenyl)-4,5-dihydroimidazole, or a pharmaceutically acceptable salt thereof, and an anti-cancer drug such that the effect of the anti-cancer drug is potentiated. A material aspect is a pharmaceutical composition useful for treatment of a cancer comprising 2,4,5-tri(4-methoxyphenyl)-4,5-dihydroimidazole, or pharmaceutically acceptable salt thereof, in combination with an anti-cancer drug. A yet further aspect is a method for controlling cancer metastasis in an organism having a cancer comprising administering to the organism 2,4,5-tri(4-methoxyphenyl)-4,5-dihydroimidazole, or a pharmaceutically acceptable salt thereof.

The present invention is useful in cancer treatments.

Notably, this invention can provide excellent potentiation effects. It may further provide such with a good toxicity profile as well. And more, this invention may control cancer metastasis to a notably effective degree.

Further advantages attend this invention as well.

DRAWINGS

The drawings form part of the specification hereof.

FIG. 1 is a graph of cell density (mean percent of control) on the ordinate vs. daunorubicin concentration on the abscissa, which shows the effect of trans-2,4,5-tri(4-methoxyphenyl)-4,5-dihydroimidazole, numerically identified 11948, on daunorubicin toxicity in K562R/III cells at certain concentrations. The potentiator verapamil 1000 is a comparative and is not of this invention. Daunorubicin 100 is also illustrated.

FIG. 2 is a graph of cell density (relative percent of control) on the ordinate vs. daunorubicin concentration on the abscissa, which shows the effect of trans-2,4,5-tri(4-methoxyphenyl)-4,5-dihydroimidazole, numerically identified 11948, on daunorubicin toxicity in K562R/III cells at certain concentrations. The potentiator verapamil 1000 is a comparative and is not of this invention. Daunorubicin 100 is also illustrated.

ILLUSTRATIVE DETAIL

The terms "potentiating" or "potentiate" or "potentiated" and so forth refer herein to the ability of a compound or composition to circumvent anti-cancer drug resistance of an anti-cancer drug resistant or an MDR cell line. A cell line known in the art, which is useful for determining potentiation of a compound or composition, is the K562/III leukemia cell line, employing resistant vs. nonresistant cell types. See, Ahmed & Vasanthakumar, *Eur. J. Cancer Clin. Oncol.* 23:1329-36 (1987). An IC50 value can be used to quantitate potentiating effect. The IC50 value is defined as the concentration of drug inhibiting the growth of cells to such an extent that their growth is reduced to one-half that observed under drug-free conditions.

The term "anti-cancer drug effect" refers herein to a reduction of cell density caused by a drug, without potentiator candidate, in a suitable cell sample. The IC50 value as generally described above can be employed to quantitate the anti-cancer drug effect.

The term "administering" and so forth refers herein to suitably providing an amount of compound or composition in vitro or in vivo to a subject so that a therapeutic effect might result. The administering can be by mere contact of the components with a cell line, or can be by conventional dosage formats as for a mammalian subject. The conventional dosage formats include the ingestion of an oral or sublingual dosage form such as a powder, sample of beads, tablet, capsule, syrup or dragee, the injection of an intravenous solution or colloidal mixture, the application of a transdermal or other external preparation such as a solution, creme, gel or other ointment, and/or the implantation of a rapid or sustained release device.

The term "subject" refers herein to an organism, or organ, organ system or cell line of an organism, which has a cancer cell line living therein or is cancerous. As such, the subject may be treated in vitro or in vivo. The subject is desirably a mammal, to include a human patient with in vivo treatment being undertaken.

The term "general concurrence" refers herein to administering of the 2,4,5-tri(4-methoxyphenyl)-4,5-dihydroimidazole, or pharmaceutically acceptable salt thereof, and the anti-cancer drug during at least the same general time frame, if not concurrently. Simultaneous administration of the 2,4,5-tri(4-methoxyphenyl)4,5-dihydroimidazole, or pharmaceutically acceptable salt thereof, and the anti-cancer drug can generally be provided by administration of composition embodiments of this invention. However, it may be desirable to administer the 2,4,5-tri(4-methoxyphenyl)-4,5-dihydroimidazole, or pharmaceutically acceptable salt thereof, at a different time than the administration of the anti-cancer drug, for example, after the anti-cancer drug is administered. This may be effected by separate administrations of the 2,4,5-tri(4-methoxyphenyl)-4,5-dihydroimidazole, or pharmaceutically acceptable salt thereof, and the anti-cancer drug or by delayed release of the 2,4,5-tri(4-methoxyphenyl)-4,5-dihydroimidazole, or pharmaceutically acceptable salt thereof, or the anti-cancer drug in relation to the other in composition embodiments of this invention.

The term "anti-cancer drug" refers herein to a compound or composition which is cytotoxic, particularly to include towards cancer cells or cancerous tissue. The anti-cancer drug may be selected from such types of compounds as anthracyclines, vinca alkaloids, or cis-platinum compounds to include coordination compounds thereof. Desirably, the anti-cancer drug is an anthracycline, e.g., daunorubicin, or a vinca alkaloid, e.g., vincristine or vinblastin.

The term "control" refers herein to a regulation. The regulation may be by partial or total cessation.

"2,4,5-Tri(4-methoxyphenyl)-4,5-dihydroimidazole" refers herein to the amarine (cis) and isoamarine (trans) configurations of this compound. The cis and trans nomenclature refers to configurations about the 4- & 5-positions (carbon atoms) of the heterocyclic ring.

Preferably, the trans-isomer is employed in this invention. The trans-isomer may be termed W-11948.

The desired compound can be prepared as follows. 4-Methoxybenzaldehyde is reacted with ammonium hydroxide to yield 4-{di-[(4-methoxybenzyl)imino]}methylanisole. In toluene, the application of heat to this compound yields cis-2,4,5-tri(4-methoxyphenyl)-4,5-dihydroimidazole. In dimethylformamide, the further reaction of this cis-compound with sodium hydride yields trans-2,4,5-tri(4-methoxyphenyl)4,5-dihydroimidazole.

Pharmaceutically acceptable salts of 2,4,5-tri(4-methoxyphenyl)-4,5-dihydroimidazole may be selected from among hydrochlorides, sulfates, fumerates, maleates, citrates, and so forth. Thus, the pharmaceutically acceptable salt may be a hydrochloride.

2,4,5-Tri(4-methoxyphenyl)-4,5-dihydroimidazole, or pharmaceutically acceptable salt thereof, can be employed as a cancer drug potentiator. It thus administered to the subject in general concurrence with an amount of an anti-cancer drug such that the effect of the anti-cancer drug is potentiated. Accordingly, as is understood in the art, a suitable dosage or dosage regimen is employed to obtain the desired effect of the components employed in relation to the subject. Amounts of the 2,4,5-tri(4-methoxyphenyl)-4,5-dihydroimidazole, or pharmaceutically acceptable salt thereof, can thus vary in relation to amounts of the anti-cancer drug employed, but total drug dosages can be smaller than corresponding dosages of the anti-cancer drug alone. Therefore, with respect to composition embodiments of this invention, unit dosage formulations can be made accordingly smaller, oftimes substantially and surprisingly so, than corresponding unit dosage formulations of the anti-cancer drug if it were generally formulated alone.

In making the composition embodiments of this invention, methods known in the art can be employed. These include well-known powder-making methods, bead-making methods, tablet-making methods, capsule-making methods, syrup-making methods, and dragee-making methods, to include methods for delayed release of one or more of the medicaments of this invention as may be appropriate, methods for the making of an intravenously-injectable solution or colloidal mixture, methods for the making of a sustainably-releasing implantable article or device, methods for the making of an ointment such as a creme or a gel, and methods for the making of a composition suitable for transdermal application of components with the aid of a suitable carrier. Accordingly, composition embodiments of this invention can have suitable adjuvant(s) therewith to help achieve the desired end dosage form provided.

2,4,5-Tri(4-methoxyphenyl)-4,5-dihydroimidazole, or pharmaceutically acceptable salt thereof, can be employed as an antimetastasis agent. It thus administered to the subject in order to control metastasis. It may be administered alone. Alternatively, it may be administered in combination with, to include in general concurrence with, an anti-cancer drug. Accordingly, as is understood in the art, a suitable dosage or dosage regimen is employed to obtain the desired effect of the components employed in relation to the subject.

In general, the better potentiating effect a combination has, the more likely it is that this combination will be better in controlling cancer metastasis. By the practice of this aspect of this invention, cancer metastasis can be generally controlled. Preferably, the control is of a substantial nature.

The following further illustrates this invention. Therein, parts and percentages are by weight unless otherwise specified.

Example with Comparative

Samples of both sensitive and resistant K562/III cells were prepared by the method of Ahmed & Vasanthakumar, supra. The resistant cells were used as one form of control. The cells were suspended in a mixture of nine parts RPMI 1640 media (Hazelton Biologics, Inc.) and one part fetal bovine serum (FBS) (Hazelton Biologics, Inc.) at a concentration of 500,000 cells per mL.

To determine chemotherapeutic activity, individual samples were prepared and evaluated as follows:

To a mixture of 3.8 mL of the 1640 media and 0.38 mL of the FBS was added 0.1 mL of a mixture of daunorubicin at various concentrations in sterile water and 0.1 mL of a mixture of potentiator candidate at a concentration of 0.5 mM in the 1640 media. To the foregoing mixture was then added 1 mL of the cell suspension. A control having only the 0.1 mL of the daunorubicin mixture with 0.1 mL of the sterile water was similarly prepared. The resultant sample or control volumes were each 5 mL total.

The samples and controls were incubated for 48 hours at 37 degrees C. in the dark under an atmosphere of 5 percent carbon dioxide and 95 percent oxygen. At the end of this incubation, the samples and controls were counted by the Coulter counter method to determine cell densities. These cell densities provided the IC50 values reported. Mean IC50 and relative (rel.) IC50 values were calculated. Mean IC50 values were calculated by standard methods. Rel. IC50 values were calculated by dividing the IC50 values obtained for a particular treatment by the IC50 value of daunorubicin to obtain a quotient, and multiplying the quotient by the average of all IC50 values for all daunorubicin samples. This takes into account the various activities of different daunorubicin lots. Both mean and rel. IC50 values for daunorubicin for 11 trials were 1465±299.

Table I lists results. The parenthetical number (#) is the number of trials carried out and used in determining the mean and rel. IC50 values.

TABLE I

| Compound | Mean IC50 (#) | Rel. IC50 (#) |
|---|---|---|
| W11948 (free base) | 413 ± 4 (2) | 485 ± 43 (2) |
| Verapamil (comparative) | 333 ± 97 (5) | 329 ± 70 (5) |

See also, FIGS. 1 & 2.

Conclusion

The present invention is thus provided. Numerous adaptations and modifications can be effected by those skilled in the art within the spirit of this invention, the scope of which is particularly pointed out by the following distinctly claimed subject matter.

What is claimed is:

1. A pharmaceutical composition useful for treatment of a cancer comprising, 2,4,5-tri (4-methoxyphenyl)-4,5-dihydroimidazole, or pharmaceutically acceptable salt thereof, in combination with daunorubicin.

* * * * *